US009164078B2

(12) United States Patent
Min et al.

(10) Patent No.: US 9,164,078 B2
(45) Date of Patent: Oct. 20, 2015

(54) PROCESS FOR PREDICTING HEMATOCRIT OF WHOLE BLOOD USING IR LIGHT

(71) Applicant: Fenwal, Inc., Lake Zurich, IL (US)

(72) Inventors: Kyungyoon Min, Kildeer, IL (US); Benjamin Kusters, Racine, WI (US); Christopher Wegener, Libertyville, IL (US)

(73) Assignee: Fenwal, Inc., Lake Zurich, IL (US)

( * ) Notice: Subject to any disclaimer, the term of this patent is extended or adjusted under 35 U.S.C. 154(b) by 343 days.

(21) Appl. No.: 13/788,164

(22) Filed: Mar. 7, 2013

(65) Prior Publication Data

US 2013/0334420 A1    Dec. 19, 2013

Related U.S. Application Data

(60) Provisional application No. 61/660,050, filed on Jun. 15, 2012.

(51) Int. Cl.
*G01N 33/49* (2006.01)
*A61B 5/145* (2006.01)
*A61B 5/1455* (2006.01)
*G01N 21/3577* (2014.01)

(52) U.S. Cl.
CPC ............ *G01N 33/49* (2013.01); *A61B 5/14535* (2013.01); *A61B 5/14557* (2013.01); *G01N 21/3577* (2013.01)

(58) Field of Classification Search
CPC ................ G01N 21/35; G01N 21/359; G01N 2015/0065; G01N 2015/0073; A61M 2205/331
USPC ................ 250/341.5, 339.11, 339.12, 338.1; 210/645–347, 748.08; 604/4.01, 6.08
See application file for complete search history.

(56) References Cited

U.S. PATENT DOCUMENTS

| | | | |
|---|---|---|---|
| 5,328,822 A * | 7/1994 | McKinney et al. | 435/4 |
| 5,487,870 A * | 1/1996 | McKinney et al. | 422/73 |
| 5,734,464 A * | 3/1998 | Gibbs | 356/39 |
| 6,064,474 A * | 5/2000 | Lee et al. | 356/39 |
| 6,294,094 B1 | 9/2001 | Muller et al. | |
| 6,419,822 B2 | 7/2002 | Muller et al. | |
| 7,170,591 B2 * | 1/2007 | Ohishi et al. | 356/39 |
| 7,608,043 B1 * | 10/2009 | Lee et al. | 600/439 |
| 2002/0026110 A1 * | 2/2002 | Parris et al. | 600/347 |
| 2002/0085951 A1 * | 7/2002 | Gelfand et al. | 422/44 |
| 2003/0210390 A1 * | 11/2003 | O'Mahony et al. | 356/218 |
| 2003/0211927 A1 * | 11/2003 | Cantu et al. | 494/3 |
| 2004/0057037 A1 * | 3/2004 | Ohishi et al. | 356/39 |
| 2004/0087860 A1 * | 5/2004 | Lee et al. | 600/468 |
| 2006/0229531 A1 * | 10/2006 | Goldberger et al. | 600/573 |
| 2008/0088820 A1 * | 4/2008 | Muller | 356/39 |
| 2012/0065482 A1 * | 3/2012 | Robinson et al. | 600/309 |

FOREIGN PATENT DOCUMENTS

WO    WO 2012/125460 A1    9/2012

* cited by examiner

*Primary Examiner* — Marcus Taningco
*Assistant Examiner* — Djura Malevic
(74) *Attorney, Agent, or Firm* — Cook Alex Ltd.

(57) ABSTRACT

A separation device is disclosed along with systems and methods employing the device in blood processing procedures. In one embodiment, a spinning membrane separator is provided. Automated systems and methods are disclosed for separating a unit of previously-collected whole blood into selected blood components, such as concentrated red cells and plasma, including prediction of the hematocrit of the whole blood using a light source and an optical sensor.

17 Claims, 6 Drawing Sheets

EXAMPLE OF EXPERIMENTAL DATA WHICH CORRELATES IR LIGHT REFLECTED BY BLOOD TO THE HCT OF THE BLOOD

PROCESS FOR PREDICTING HEMATOCRIT OF WHOLE BLOOD USING IR LIGHT

FIELD OF THE DISCLOSURE

The present application is related generally to methods and systems for collecting and processing blood and, more particularly to methods and systems for predicting the hematocrit of whole blood as part of a blood collection and separation procedure.

BACKGROUND

In various blood collection, processing and therapeutic procedures, certain process parameters that are based on the percentage of red blood cells, or hematocrit, in the blood must be established. For example, traditional blood collection relies primarily on the collection of whole blood from healthy donors through blood drives or from donor visits to blood centers or hospitals and the like. Blood may be collected "manually" or in an automated fashion such as by apheresis. In typical manual collection, whole blood is collected by simply flowing it, under the force of gravity and venous pressure, from the vein of the donor into a collection container. The amount of whole blood drawn is typically a "unit," which is about 450 ml. In apheresis, whole blood is withdrawn from a donor (or patient) under the action of a pump on an apheresis device to which the donor remains attached during the procedure.

Whether manual or automated, modern blood collection typically employs a pre-assembled arrangement or kit of tubing and containers or bags, including a flexible plastic primary container or bag for receiving a unit of whole blood or blood component from a donor and one or more "satellite or other" containers or bags. The blood is first collected in the primary container, which also contains an anticoagulant (typically containing sodium citrate, phosphate and dextrose—often referred to as CPD) or is otherwise combined with an anticoagulant during withdrawal from the donor. A preservative (often called an "additive solution" or AS) may be included as part of a larger assembly of bags and tubes that are used in processing after the blood is collected.

After collection of a unit of whole blood in a manual procedure, it is common practice in blood banking to transport the unit of whole blood to a blood processing laboratory, commonly referred to as a "back lab," for further processing of the blood into its various components. In order to effectively and efficiently separate the whole blood into its components, process parameters based on the hematocrit of the whole blood must be established. The hematocrit of the blood being processed is also important in establishing process parameters in various automated apheresis procedures, such as red blood cell collection and/or therapeutic red blood cell and plasma exchanges.

It is known to use an infrared (IR) light source and optical sensor to sense changes in the hematocrit of blood during processing. See, U.S. Pat. No. 6,419,822, which is incorporated herein by reference. While the IR sensor and system described therein has worked satisfactorily, information about the characteristics of the whole blood, including the hematocrit, is input by the operator.

By way of the present application, a method and system for predicting the hematocrit of blood as part of a blood processing procedure using a light source and optical sensor are provided that does not require any prior knowledge of the characteristics of the blood being processed.

SUMMARY OF THE DISCLOSURE

The present subject matter has a number of aspects which may be used in various combinations, and the disclosure of one or more specific embodiments is for the purpose of disclosure and description, and not limitation. This summary highlights only a few of the aspects of this subject matter, and additional aspects are disclosed in the drawings and the more detailed description that follows.

In accordance with one aspect of the disclosure, a method for predicting the hematocrit of blood in a blood processing procedure is provided in which blood is processed into one or more blood components with a single-use processing kit. "Blood" as used herein refers broadly to either whole blood, to a blood product including red blood cells, or to concentrated red blood cells. The processing kit includes a flow path or tubing through which the whole blood is flowed and a reusable hardware module onto which the processing kit is mounted, with the hardware module including a sensing field defined by an infrared light source and an infrared reflectance sensor that receives a segment of the tubing.

The method comprises loading the processing kit onto the hardware module with a segment of the flow path or tubing positioned in the sensing field defined by the infrared light source and the infrared reflectance sensor. An infrared reflectance measurement of the segment of the tubing when there is either no fluid or a non-reflecting fluid (typically a clear fluid) within the tubing is obtained. Blood is then flowed through the segment of the tubing, and an infrared reflectance measurement of the segment of the tubing filled with blood is obtained. The natural log of the infrared reflectance measurement attributable to the presence of blood and the segment of the tubing is derived, and this value is inputted into a correlation equation to predict the hematocrit of the blood. The predicted hematocrit is then outputted so that it may be made known to a user or otherwise become available for establishing process parameters for the system's operating algorithm.

In keeping with another aspect of the disclosure, a method for creating the correlation equation for a processing kit is provided. The method comprises separately flowing a plurality of samples of blood through the segment of tubing of the processing kit, with each of the samples having a known hematocrit that is different from the hematocrit of the other samples. An infrared reflectance measurement of the segment of the tubing filled with the blood is obtained for each sample. The natural log of the infrared reflectance measurements attributable to each sample is derived, and the correlation equation is derived based on a linear fit of a plot of the known hematocrit for each sample and the natural log of the infrared reflectance measurement for each sample. The correlation equation may be developed at a time prior to the processing of the blood and preprogrammed into a controller for the reusable module.

In accordance with another aspect of the disclosure, a reusable hardware module is provided for use with a single-use processing kit. The reusable module comprises a programmable controller with an input for receipt of a first signal corresponding to an infrared reflectance measurement attained from the processing kit and then an output for transmitting a second signal corresponding to a predicted hematocrit for the blood being processed. The programmable controller is configured to derive the natural log of the infrared reflectance measurement, input the natural log of the infrared reflectance measurement into a predetermined correlation equation, generate the second signal corresponding to the predicted hematocrit, and transmit the second signal to an interface by which it may be perceived by a user.

In accordance with another aspect of the disclosure, an automated blood separation system is provided that may comprise both the disposable single-use processing kit and the reusable hardware module including the programmable module that is configured to cooperate with and control fluid flow through the processing kit. The processing kit includes a blood fluid flow path with a blood inlet for connection to a source of blood, such as a primary container of whole blood previously collected from a donor, or the donor himself. The kit may also include a cell preservation solution flow path with an inlet for connection to a source of cell preservation solution. The processing kit also includes a separator, which may be either a centrifugal separator or a spinning membrane separator. While a spinning membrane separator is described below in connection with the specific embodiments, the fluid circuit is not so limited.

The programmable controller controls the processing of blood through the processing kit, and, if desired, controls the speed of the separator, and/or any associated pumps and/or clamps for controlling flow rates of fluid through the processing kit.

BRIEF DESCRIPTION OF THE DRAWINGS

These and other features of the present subject matter are described in the following detailed description and shown in the attached figures, of which.

DETAILED DESCRIPTION

A more detailed description of a process for predicting the hematocrit of blood in accordance with the present disclosure and its use in various automated systems is set forth below. As used herein, the term "automated" may refer to the processing of a previously manually collected unit of whole blood under the direction of a pre-programmed controller of a processing device. The term "automated" may also refer to a fully automated processing system and processing system, such as an apheresis system, where the donor or patient remains "connected" to the apheresis device during the procedure. Thus, it should be understood that description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figure 1:
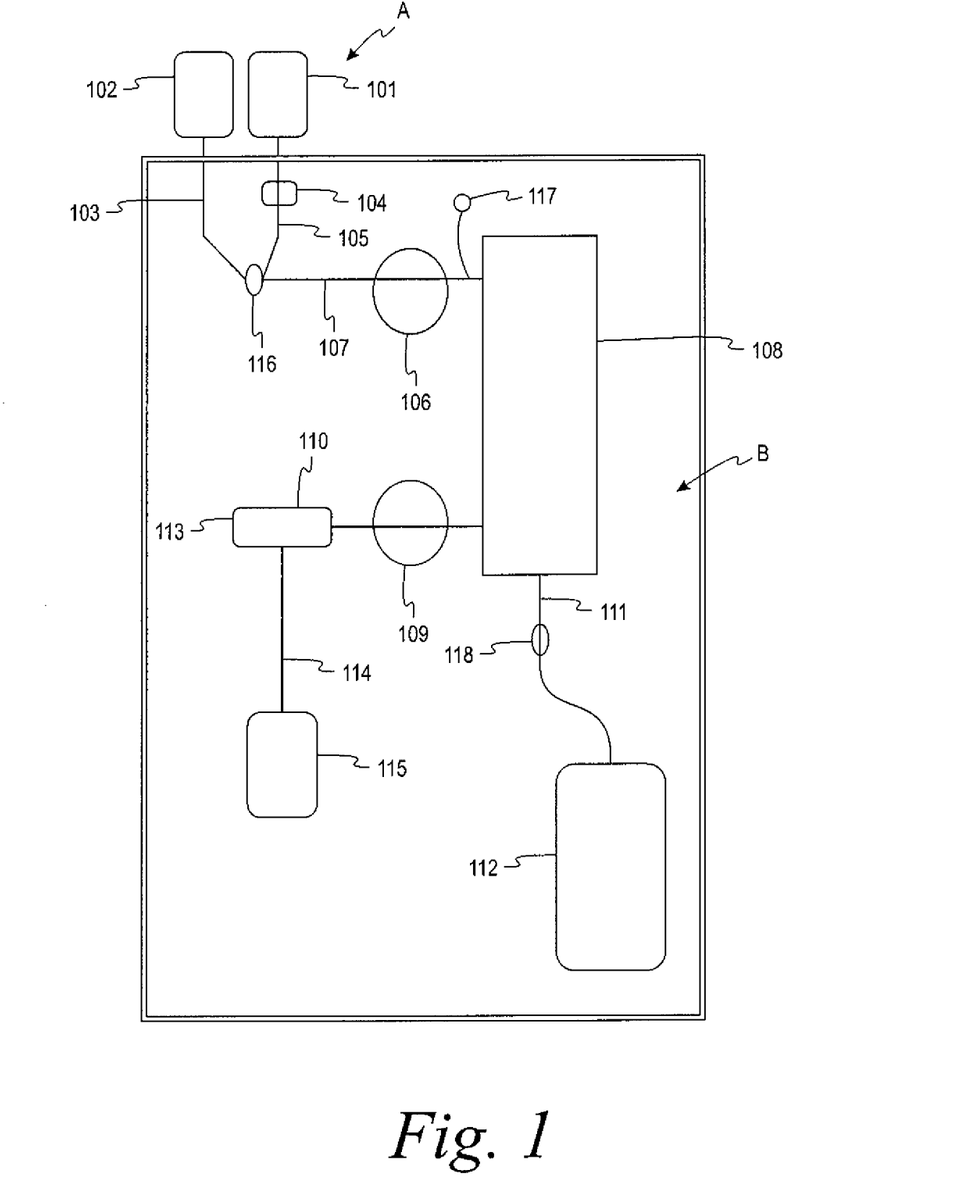
FIG. 1 is a schematic view of an automated blood separation system for processing blood including a disposable fluid flow circuit module and a durable controller or control module with the fluid flow circuit module assembled thereon.
Figure 5:
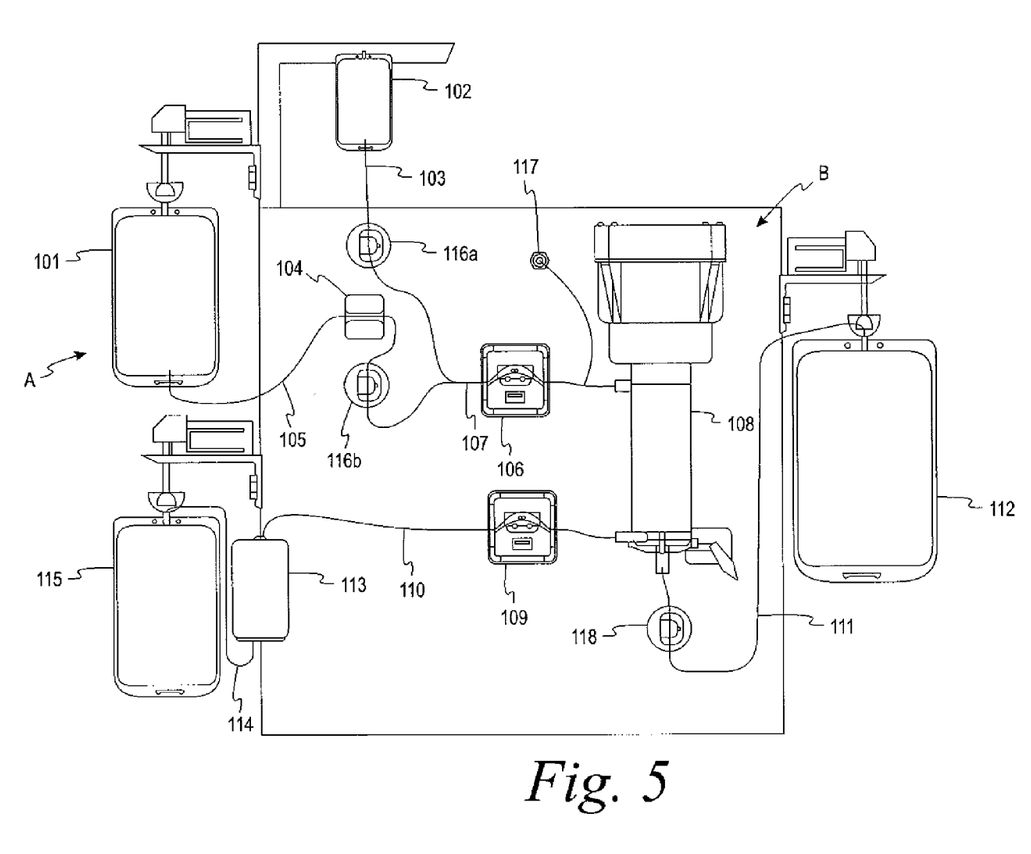
FIG. 5 is similar to FIG. 1 but a somewhat more detailed view of components of a disposable fluid flow circuit or module and a durable controller module.

Turning now to FIG. 1, a disposable fluid flow circuit or module A and a reusable durable controller or module B configured to cooperate with and control flow through the fluid circuit A are schematically illustrated. The disposable fluid circuit A as illustrated in FIG. 1 includes various components interconnected by flexible plastic tubing defining flow paths between the components. The circuit is preferably fully pre-assembled and pre-sterilized (with the possible exception of the unit of whole blood container and the cell preservative container). More specifically, the illustrated disposable circuit in FIG. 1 is for the processing of previously collected whole blood. The circuit includes whole blood container 101, a cell preservation solution container 102, blood component separator 108, plasma collection container 112, optional leukocyte reduction filter 113, and red cell collection container 115. While not illustrated in FIG. 1, the reusable module B may have hangers with associated weigh scales for supporting any or all of the containers 101, 102, 112 and 115 as seen in FIG. 5.

The whole blood collection container 101 may be any suitable container, but is typically a flexible plastic pouch or bag in which approximately 450 ml of whole blood have been previously collected. The container 101 may be either part of a separate system during collection and then joined to the rest of the fluid circuit A or actually part of the circuit A at the time of collection. At the time collection, in accordance with customary procedure, the whole blood is mixed with an anticoagulant located in the primary container to prevent premature coagulation. Accordingly, "whole blood" as used herein includes blood mixed with anticoagulant.

Flexible plastic tubing 105 is attached to the whole blood collection container, such as by a sterile connection device or other suitable attachment mechanism, and defines a whole blood fluid flow path between the whole blood container 101 and a junction with cell preservative solution tubing 103, which extends from the cell preservation solution container 102 to the flow path junction. The flow path junction between the whole blood flow path and all preservative flow path is located at inlet clamp 116. From the junction, the flow path extends through tubing 107 to an inlet port in the separator 108.

As shown in FIG. 1, the separator housing has an outlet that communicates with the gap between the housing and rotor and with concentrated red cell flow path tubing 110 for withdrawing concentrated red cells from the separator gap. In addition, the housing includes an outlet from the rotor that communicates with the side of the membrane facing away from the gap (for example, the interior of the rotor) and communicates with plasma flow path tubing 111.

For reducing the number of leukocytes that may be present in the red cells, the disposable fluid flow circuit A optionally includes a leukocyte reduction filter 113, which may be of any suitable well known construction for removing leukocytes from concentrated red cells without unduly causing hemolysis of red cells or reducing the number of red cells in the collected product. The concentrated red cells flow from the leukocyte reduction filter 113 through a continuation 114 of the concentrated red cell flow path into storage container 115 which may be of any suitable plastic material compatible with red cell storage.

The reusable or durable controller module B, as shown in the FIG. 1 schematic, preferably includes a hematocrit sensor 104 comprising an infrared (IR) light source and an optical sensor for detecting the hematocrit and the whole blood flowing from the whole blood container 101. The hematocrit sensor is preferably as described in U.S. Pat. No. 6,419,822, referred to above.

Figure 6:
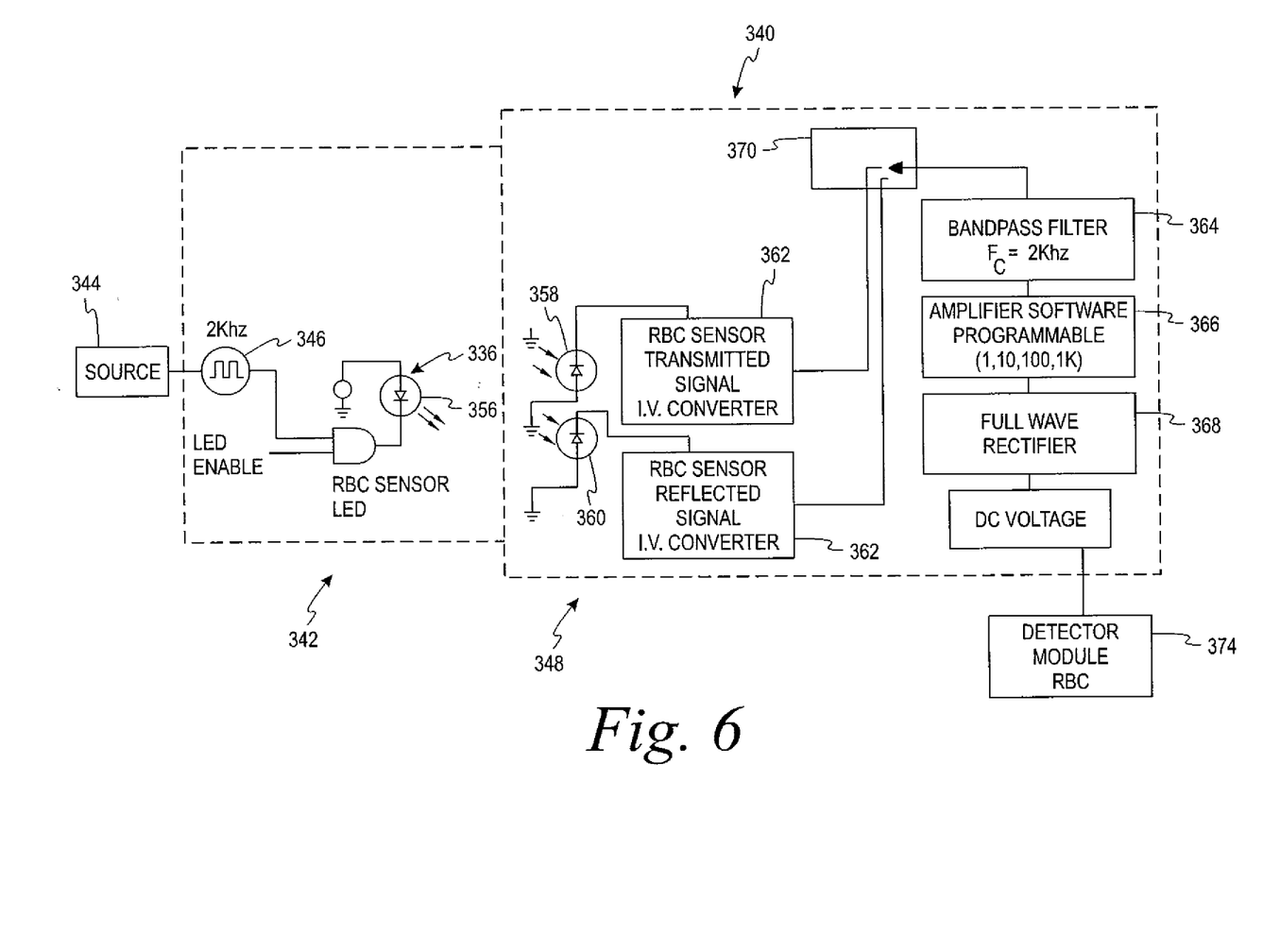
FIG. 6 is a schematic view of a hematocrit sensor that may be used in connection with the methods and systems described herein.

As seen in FIG. 6, sensing circuit 340 comprises sensor 336. The sensor 336 includes one red LED 356 and two photodiodes 358 and 360. The photodiode 358 measures transmitted light, and the photodiode 360 measures reflected light.

The sensing circuit 340 also includes a receiver circuit 348 coupled to the photodiodes 358 and 360. The receiver circuit 348 includes, for each photodiode 358 and 360, a dedicated current-to-voltage (I-V) converter 362. The remainder of the receiver circuit 348 includes a bandpass filter 364, a programmable amplifier 366, and a full wave rectifier 368. These components 364, 366, and 368 are shared, e.g., using a multiplexer.

Ambient light typically contains frequency components less than 1000 Hz, and electromagnetic interface (EMI) typically contains frequency components above 2 Khz. The modulator 346 modulates the current at a frequency below the EMI frequency components, e.g., at about 2 Khz. The bandpass filter 364 has a center frequency of about the same value, i.e., about 2 Khz. The sensor circuit 340 eliminates frequency components above and below the ambient light source and EMI components from the sensed measurement. In this way, the sensing circuit 340 is not sensitive to ambient lighting conditions and EMI.

More particularly, transmitted or reflected light from the tube containing the fluid to be measured is incident on photodiodes 358 and 360. Each photodiode produces a photocurrent proportional to the received light intensity. This current is converted to a voltage. The voltage is fed, via the multiplexer 370, to the bandpass filter 364. The bandpass filter 364 has a center frequency at the carrier frequency of the modulated source light (i.e., 2 Khz in the illustrated embodiment).

The sinusoidal output of the bandpass filter 364 is sent to the variable gain amplifier 366. The gain of the amplifier is preprogrammed in pre-established steps, e.g., ×1, ×10, ×100, and ×1000. This provides the amplifier with the capability to respond to a large dynamic range.

The sinusoidal output of the amplifier 366 is sent to the full wave rectifier 368, which transforms the sinusoidal output to a DC output voltage proportional to the transmitted light energy.

Photon wavelengths in the near infrared spectrum (NIR) (approximately 540 nm to 1000 nm) are suitable for sensing red blood cells, as their intensity can be measured after transmission through many millimeters of blood.

The sensor circuit 340 includes a red blood cell detection module 374. The detection module 374 analyses sensed optical transmissions of the second sensor 336 to discern the hematocrit and changes in the hematocrit of red blood cells existing the processing chamber.

The detection module 374 considers that the attenuation of a beam of monochromatic light of wavelength λ by blood may be described by the modified Lambert-Beer law, as set forth in U.S. Pat. No. 6,419,822.

The optical density due to absorption by red blood cells changes linearly with hematocrit for the hematocrit range of at least 10 to 90. Thus, with the sensor 336 so configured, the detection module can treat the optical density of the sample for the reflected light to be a linear function of hematocrit.

This arrangement relies upon maintaining straightforward measurement geometries. No mirrors or focusing lenses are required. The LED or photodiode need not be positioned at an exact angle with respect to the blood flow tube. No special optical cuvettes are required. The sensor 336 can interface directly with the transparent plastic tubing.

In keeping with the methods and systems disclosed herein, a predicted hematocrit for the whole blood may be obtained without any prior knowledge of the characteristics of the whole blood. The system and method obtain reflectance measurements, derive a $LN_{IRreflectance}$ value, and then input that value into a correlation equation which will output a predicted hematocrit. The position of the calibration curve with respect to the $LN_{IRreflectance}$ axis can vary depending on the characteristics of the tubing (ie. wall thickness, color, etc.), the solution the blood is suspended in (plasma only, plasma+CPD, plasma+ACD, etc.), and the flow rate at which the blood is passing through the tubing. Therefore, separate correlation curves and equations are required for each unique processing kit/durable module combination.

Figure 2:
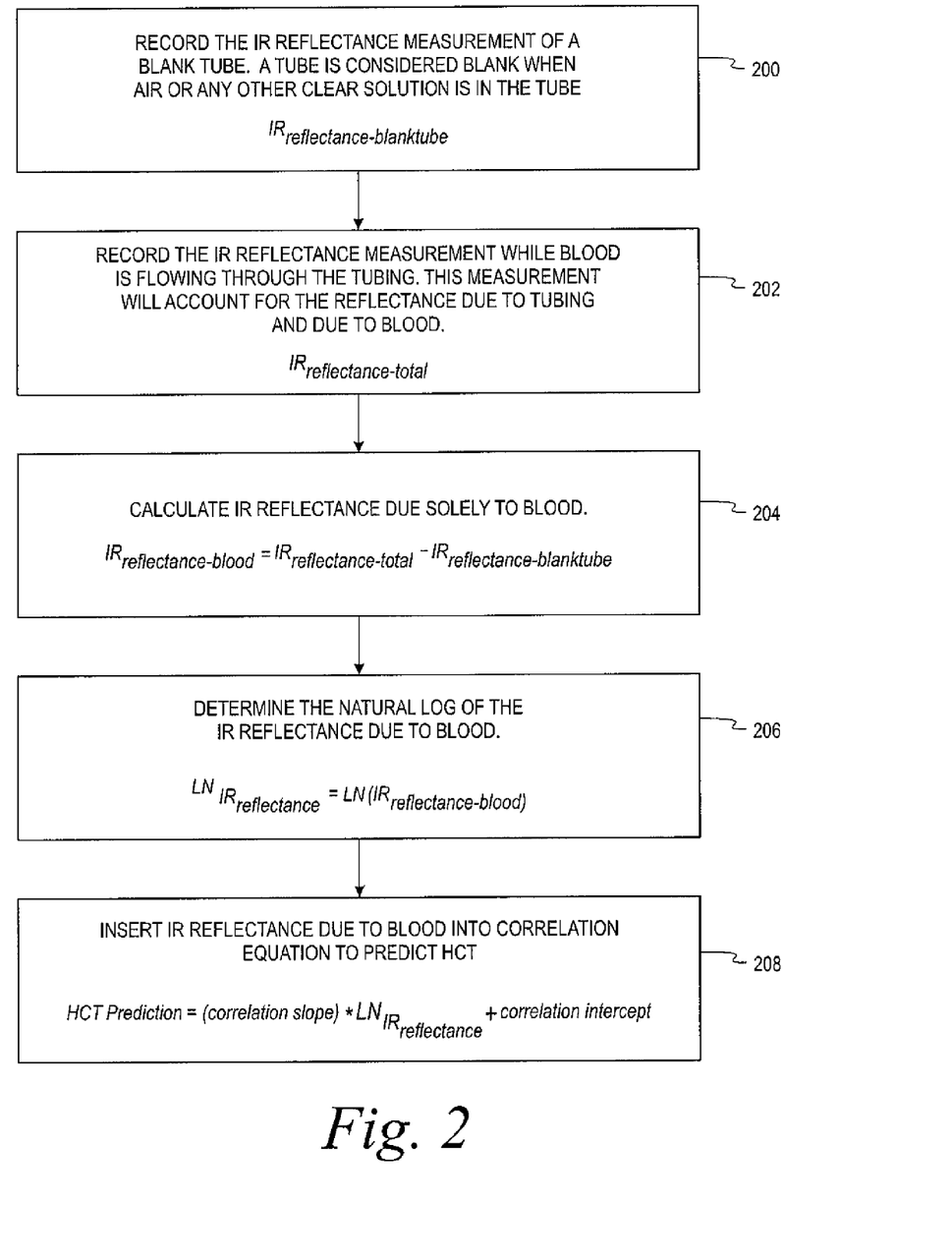
FIG. 2 is a flow chart showing the steps for predicting hematocrit of blood in accordance with the methods and systems disclosed herein.

With reference to FIG. 2, there is seen a flow chart illustrating various steps of the method. A predicted hematocrit is determined by first recording an IR reflectance measurement while air or any other clear (i.e., non-reflecting) fluid (saline, adsol, ACD, etc.) is within the tubing (Box 200). This calibration measurement, sometimes referred to as a "blank calibration," represents the extent to which the tubing alone reflects IR light. $IR_{reflectance-blanktube}$ is thus obtained. The amount of reflectance has been found to vary greatly depending on how the tubing of the processing kit is mounted into the system. Thus, the segment of the flow path received in the sensing field may preferably include a chamber, such as a cuvette, made of an optically-clear material, such as polycarbonate, that provides more consistent reflectance. Although blood of the same hematocrit will produce a similar amount of IR reflectance, the sensor may detect different amounts of overall reflectance due to the variation between tubing sets of the light reflected by the tubing. Therefore, if the tubing reflectance is not accounted for by the initial calibration, the same blood passing through two different tubing sets may produce different overall reflectance measurements. Specifically, initiating the procedure by calibrating with a "blank" tube allows the amount of light reflected by the tubing to be accounted for and "zeroed" out of the reflectance measurement recorded when blood is within the tube.

After the IR reflectance due to the tubing is taken into account, blood is flowed through the tubing past the IR system, and IR reflectance measurements are taken while blood is flowing through the system (Box 202). The amount of IR reflectance measured while blood flows through the tubing ($IR_{reflectance-total}$) in addition to the amount of IR reflectance measured while the tubing was 'blank' ($IR_{reflectance-blanktube}$) is representative of the IR light reflected by only the blood ($IR_{reflectance-blood}$) (Box 204). The IR reflectance of the blood alone is required to correlate hematocrit to IR reflectance. Any other source of reflectance (such as the light reflected by tubing) is unwanted in the hematocrit to IR reflectance correlation. Thus, $IR_{reflectance-blood} = IR_{reflectance-total} - IR_{reflectance-blanktube}$.

Lastly, the Natural log of the $IR_{reflectance-blood}$ value must be taken in order to relate IR reflectance measurements to hematocrit in a linear fashion (Box 206).

$$LN_{IR\ reflectance} = LN(IR_{reflectance-blood})$$

Figure 3:
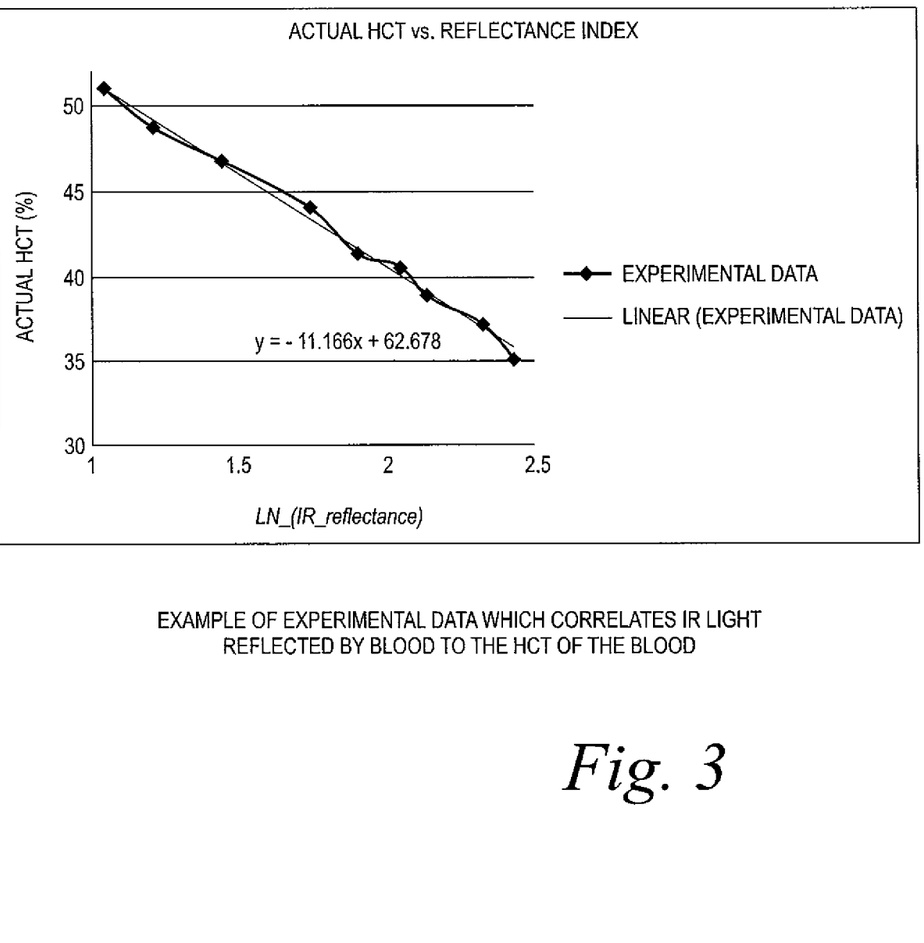
FIG. 3 is a graph of experimental data correlating the light reflected by blood to the hematocrit of the blood.

In order for the blood reflectance measurements to be useful in the prediction of hematocrit without any prior knowledge of the blood's characteristics, a correlation of hematocrit to $IR_{reflectance-blood}$ must first be generated. This is typically done once at a time prior to and place separate from the processing of the whole blood. The correlation equation is obtained by taking a number of samples of blood of known hematocrit, and correlating the hematocrits of the samples to the reflectance measurements they produce. Performing this task over a desired range of hematocrits (e.g. 35-55% for the typical whole blood range) permits generation of a correlation curve, such as that seen in FIG. 3, which is a graph of experimental data obtained using the method described herein. The linear fit to the data generates the correlation curve and the correlation equation used by the algorithm of the system to predict the hematocrit of a sample of blood (Box 208). Once a value for the predicted hematocrit of the whole blood is obtained, further parameters for processing procedure may be established, and the procedure may continue as described below.

Returning to FIG. 1, the durable reusable controller or control module B also includes an inlet clamp 116 which may be operated to control fluid from the whole blood container 101 or the cell preservative container 102 or, optionally, simultaneously and proportionally from both of the containers 101 and 102. For controlling flow of blood into the separator, the reusable module includes an inlet pump 106, which also may be of any suitable construction, and may be, for example, a peristaltic type pump which operates by progressive compression or squeezing of the tubing 107 forming the inlet flow path into the separator, a flexible diaphragm pump or other suitable pump. A pressure sensor 117 communicates with the inlet flow path between the pump 106 and the separator 108 to determine the inlet pumping pressure. The sensor may output to the control system to provide an alarm function in the event of an over-pressure condition or an under-pressure condition or both.

To control the flow rate of concentrated red cells from the separator 108, the reusable module also includes an outlet pump 109 that is associated with the outlet flow path 110, and functions in the manner similar to that described with respect to inlet pump 106. It also may be of any suitable construction such as a peristaltic pump, a flexible diaphragm or other suitable pumping structure. The plasma flow path 111 exiting the separator is preferably not controlled by a pump, and the volumetric flow rate through the plasma flow path tubing is the difference between the inlet volumetric flow rate from pump 106 and the outlet volumetric flow rate from pump 109. Reusable module B may, however, also include a clamp 118 for controlling flow of plasma through the plasma flow path tubing 111.

The disposable module A may also include a plasma collection container 112 in fluid communication with the plasma flow path for receiving plasma separated by the separator 108. Because the plasma passes through a porous membrane in the separator 108, the plasma that is collected in container 112 is largely cell free plasma and may be suitable for administration to patients, freezing for storage or subsequent processing.

Figure 4:
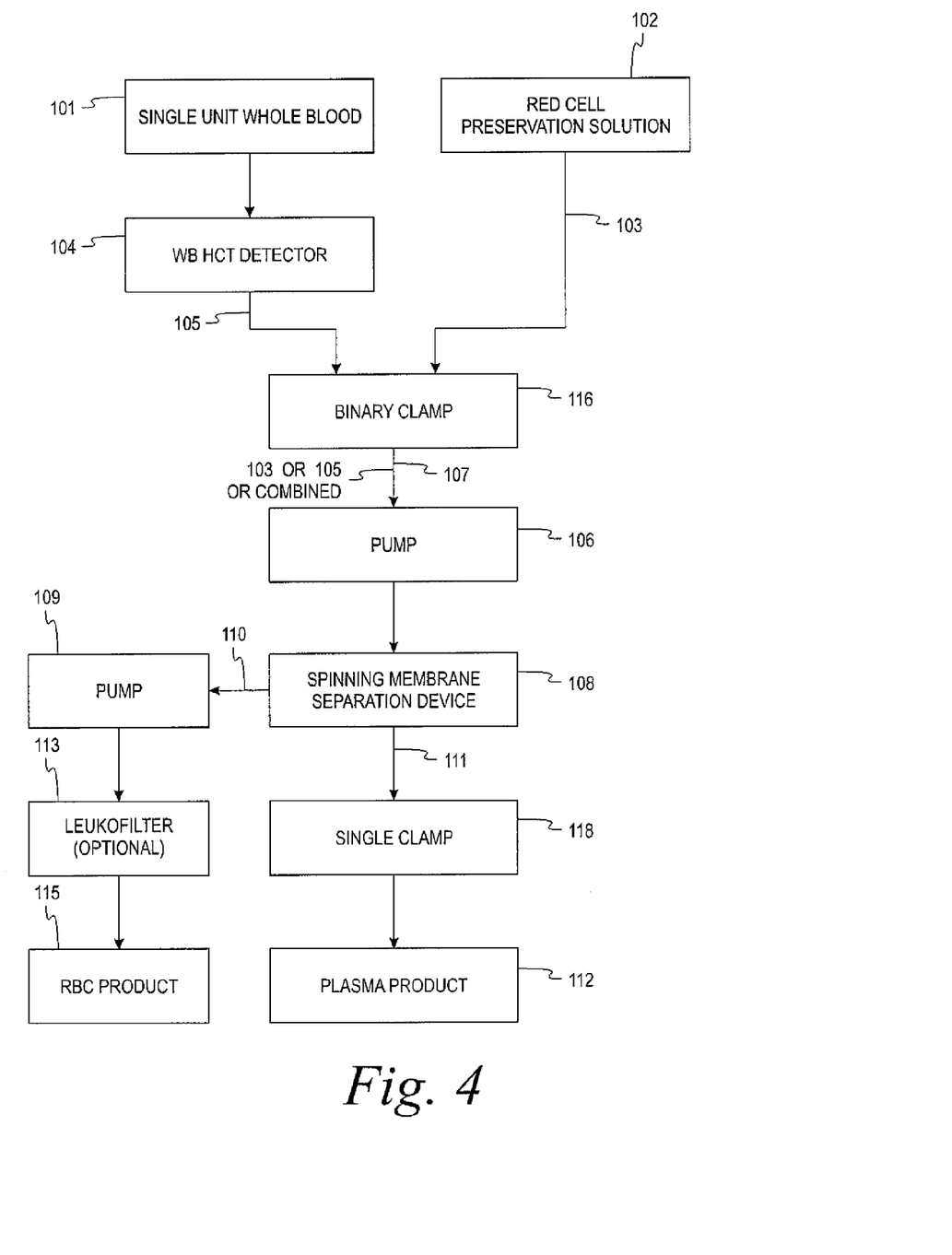
FIG. 4 is a flow diagram showing one embodiment of fluid flow through a fluid flow circuit as described herein for processing a unit of whole blood into a concentrated red cell product and a plasma product.

FIG. 4 generally shows the flow path(s) of fluid through the system illustrated in FIG. 1. Specifically, it shows flow of whole blood from the single unit whole blood container 101 through the whole blood hematocrit sensor 104, to a junction in the flow path located at the binary clamp 116. Cell preservation solution, such as a red cell preservation solution, flows from the red cell container 102 also to the junction at the binary clamp 116. Depending on the processing stage, the binary clamp allows the flow of whole blood or cell preservative downstream into the remainder of the system. Optionally, the clamp 116 could be a proportional clamp to allow a selected proportionate flow of whole blood and red cell preservative simultaneously.

From the binary clamp 116, the whole blood or cell preservative fluid flows through the inlet pump 106 and into the separation device 108. As explained earlier, the separation device employs a relatively rotating housing and rotor, at least one of which carries a membrane through which plasma is allowed to pass. In one embodiment, the membrane is carried on the surface of the rotor and plasma passes through the membrane and through internal passage labyrinth within the rotor exiting eventually to the plasma collection container 112. When the membrane is mounted on the rotor, the device is commonly referred to a spinning membrane separator, as shown in FIG. 4. However, it should be recognized that the membrane could potentially be mounted on the inside surface of the housing, facing the gap between the inside surface of the housing wall and the outer surface of the membrane, or a membrane could be carried on both the outer surface of the rotor and the inner surface of the housing so that plasma flows through membranes simultaneously, therefore potentially increasing the separation speed or performance of the separator 108. From the separator 108, the concentrated red cells flow through the housing outlet communicating with the gap between rotor and housing and through the red cell flow path 110 and the outlet pump 109, which controls the volumetric flow rate of the concentrated red cells.

While the hematocrit of the concentrated red cells removed from separator 108 may vary, it is anticipated that the hematocrit of the concentrated red cells will be approximately 80-85%. The outlet pump 109 pumps the concentrated red cells into the red cell collection container 115 and, optionally, through a leukocyte reduction filter located in the red cell flow path between the pump 109 and the collection container 115. The force of the pump pushing the concentrated red cells through the leukocyte reduction filter helps to maintain the processing time within a reasonable range, as compared, for example, to the time it would be required for gravity flow of concentrated red cells through a leukocyte reduction filter in a manual setting.

The plasma separated by the separator 108, as shown in the FIG. 4, flows from the separator device, for example, from an outlet communicating with a labyrinth of passageways within the rotor through a single control clamp 118 and to the plasma collection container 112. As noted earlier, because the plasma passes through the membrane, it is largely cell free and suitable for subsequent administration to patients, freezing, and/or for the processing, such as by fractionation to obtain plasma components for use in other therapeutic products. The system could also include a filter such as a leukocyte reduction filter in the plasma flow line 111 if desired.

FIG. 5 illustrates one version of a potential system employing both a disposable fluid circuit module A and a reusable or durable controller module B. Although shown assembled, the fluid circuit module A and durable module B have separate and independent utility and may be used with other systems as well. As can be seen in FIG. 5, the disposable module A is conveniently mounted to the face of the reusable module B, which has associated hangars or supports, some of which may be associated with weight scales, for supporting the various containers of the disposable system. The disposable module is, as indicated earlier, preferably preassembled, and pre-sterilized. The cell preservative solution container may be pre-attached as part of the disposable system or may be added later, such as by a sterile connection device or other suitable attachment. The whole blood container which contains the unit of previously collected whole blood may also be pre-attached to the pre-assembled fluid circuit or attached by way of a sterile connection device or other suitable attachment mechanism.

The face of the reusable module B includes, in this embodiment, a separate solution clamp 116*a* for controlling flow of cell preservation solution from the solution container 102, which is hung from an elevated solution support pole. The whole blood container 101 is hung from a weight scale. The weight scale may be of conventional construction and may provide a weight measurement signal that may be used by the control system of the module B for sensing the amount of whole blood that remains in the container and/or the amount of whole blood that has been processed through the system. The disposable system includes a red cell flow path 105 that extends from the whole blood container, through the hematocrit sensor 104, and through a separate whole blood clamp 116b for controlling flow of whole blood from the container into the system. The cell preservative solution flow path 103 and the whole blood flow path 105 combine at a junction, such as a v-site or y-site, upstream of the inlet pump 106. The combined flow path extends through the inlet pump and to an inlet on the separator device 108. As is visible in FIG. 5, the reusable module B includes a drive unit, such as a magnetic drive unit for causing rotation of the rotor within the separator housing without requiring drive members or components to physically extend through the housing. In this arrangement, the rotor includes a magnetically coupled drive element that is rotated by the magnetic drive unit associated with the reusable module. This system is described more fully in U.S. Pat. No. 5,194,145 to Schoendorfer, incorporated by reference herein.

The concentrated red cell outlet from the separator 108 is attached to the red cell flow path 110, which extends through outlet pump 109 and to an inlet into the optional leukocyte reduction filter 113. Filter media located between the inlet and outlet of the leukocyte reduction filter substantially removes leukocytes from the red cells. From the filter outlet, the red cell flow path tubing 114 conveys the red cells into the red cell collection container 115.

Plasma is conducted from the plasma outlet of the separator through a plasma flow control clamp 118 and into the plasma collection container 112. In a manner similar to the whole blood container, the concentrated red cell container 115 and the plasma container 112 are suspended from weight scales which may be in electronic communication with the control system of the durable or reusable module B to provide information regarding the amount of concentrated red cells and/or plasma collected from the whole blood or the rate of collection.

While this system has been illustrated with certain basic components and features as described above, this description is not intended to preclude the addition of other components, such as sensors, pumps, filters or the like as may be desired. For example, it may optionally be desired to filter plasma before it enters the plasma collection container or to omit a leukoreduction filter for red cells. Although the plasma removed from the separator 108 is largely cell free, there may be a further desire to filter the plasma for reasons of subsequent administration or processing. The present description is not intended to preclude the possible addition of further components or the deletion of one or more of the components described above.

Turning now to the processing of whole blood in the illustrated systems, the separation process begins by priming the system. "Priming" refers to the method by which the filter membrane is prepared (i.e., wetted) prior to use. It is during priming that the blank calibration of the processing kit is preferably performed as described above. Wetting with a fluid helps to displace air present in the matrix of the membrane prior to pressure-induced fluid flow through the membrane. Typically, a low viscosity non-biological fluid, such as a cell preservation solution (red cell solution such as, Adsol® solution) is used for wetting to allow the most effective displacement of air. During the prime, fluid is removed from the cell preservation solution bag 102 by the inlet pump 106 until the solution line 103, whole blood line 105, inlet line 107, and spinning membrane device 108 are completely filled with the solution. To ensure proper priming, the inlet pump 106 may move both clockwise and counterclockwise during the prime. The purpose of the solution prime is to prevent an air-blood interface from forming by creating a solution-blood interface and to wet the membrane within the separation device. Each is a measure taken to reduce the hemolysis of red blood cells.

After the system is successfully primed, the cell solution flow path 103 will be closed by the inlet clamp 116. The illustrated inlet clamp is a binary clamp that can close either the cell preservation solution flow path 103 or the whole blood flow path 107. Whole blood will then be pumped through the whole blood flow path 105 and the inlet flow path 107 by the inlet pump 106 into the separator 108. Inlet pump 106 flow rates can vary from about 10 ml/min to 150 ml/min depending on desired product outcomes for a specific procedure. As the whole blood leaves the whole blood container 101 it will pass through the whole blood hematocrit detector 104 to obtain reflectance measurements and provide a predicted hematocrit for the whole blood, as outlined above. The whole blood hematocrit value is then used for an initial control algorithm of the illustrated system. For example, with the predicted hematocrit, the control algorithm may set processing times, pump speeds, flow rates, desired end hematocrit, collection volumes, and the like.

After whole blood has filled the separator 108, the system will begin to draw plasma from the separator which separates the whole blood entering the spinning membrane device into a red cell concentrate and virtually cell free plasma. Packed red blood cells at approximately 80-85% hematocrit will be pumped out of the separator 108 through the red cell flow path 110 and into the red blood cell leukofilter 113 by the outlet pump 109. The outlet pump forces the packed red blood cells through the red blood cell leukofilter 113 and the red cell concentrate which exits the red blood cell leukofilter 13 through the red blood cell line 114 and into the red blood cell product bag 115 will be successfully depleted of white blood cells and also depleted of platelets. It is also possible to complete a whole blood automated separation without the use of a red blood cell leukofilter 113. In this case the red blood cell leukofilter 114 would be removed from the system and the red blood cell product 115 would not be depleted of white blood cells or platelets.

Throughout the procedure, plasma will flow through the plasma flow path 111 into the plasma bag 112 at a flow rate equal to the difference between the inlet pump 106 flow rate and outlet pump 109 flow rate as is currently done in other spinning membrane separation applications like that applied in the Autopheresis-C® instrument sold by Fenwal, Inc. The pressure across the membrane generated by the offset in flow rates is monitored by the pressure sensor 117. The pressure measurements are used to control the plasma flow rate using the algorithm described in U.S. patent application Ser. No. 13/095,633, filed Apr. 27, 2011 (Title: Systems and Methods of Controlling Fouling During A Filtration Procedure) hereby incorporated by reference.

The system in FIGS. 1, 4 and 5 will continue to separate packed red blood cells and plasma until the whole blood bag 101 is empty as detected by air passing through the whole blood hematocrit sensor 104. At this point the whole blood line 105 will be closed and the cell preservative solution line will be opened by the inlet clamp 116 to start the solution rinse or flush. During the solution rinse, preservative solution will be removed from the solution bag 102 and pumped into the separator 108 by the inlet pump 106. The plasma flow path 111 is closed by the plasma clamp 118 during the solution rinse. The solution rinse is used to flush any blood remaining in the system into the red blood cell product container 115. The solution rinse will also increase the red blood cell product container 115 volume to the level desired for proper red blood cell storage. After the solution rinse is finished the separation of the whole blood unit is complete. Further details of the system and process described above for the separation of whole blood are set forth in PCT/US2012/28500, filed Mar. 9, 2012, the contents of which is incorporated herein by reference.

Thus, a method and system for quickly and accurately predicting blood hematocrit without significant operator input are disclosed. The description provided above is intended for illustrative purposes only, and is not intended to limit the scope of the disclosure to any specific method, system, or apparatus or device described herein. For example, while the process of this disclosure has been described in connection with the processing of whole blood to obtain a red blood cell product, the process could be also incorporated into any blood separation device or procedure that requires the donor's hematocrit to be input. Thus, for example, where the embodiments described above and depicted in the figures are based on a system that utilizes a spinning membrane, the process and system of hematocrit detection can likewise be employed in apparatus that are based on a different separation principle such as centrifugal separation. An example of such an apparatus is the Alyx® separator available from Fenwal, Inc. of Lake Zurich. As the whole blood of the donor is pumped into the device at the start of the procedure the process described herein would be used to predict the hematocrit of the blood rather than having the operator input the hematocrit into the system. This process also has the potential to be used in a lab setting to quickly predict the hematocrit of whole blood without the use of a cell counting machine (ex. Sysmex) or spun hematocrit centrifugation processes. Further, the system and method of predicting hematocrit, as described herein, may also be used to predict the hematocrit of already separated (and concentrated) red blood cells.

The invention claimed is:

1. In a blood processing procedure in which blood is processed into one or more blood components with a single-use processing kit, the processing kit including tubing through which the blood is flowed, and a reusable hardware module onto which the processing kit is mounted, the reusable hardware module including a sensing field defined by an infrared light source and an infrared reflectance sensor that receives a segment of the tubing, a method for predicting the hematocrit of the blood comprising:
   loading the processing kit onto the hardware module with a segment of the tubing positioned in the sensing field defined by the infrared light source and the infrared reflectance sensor;
   obtaining an infrared reflectance measurement of the segment of the tubing with either no fluid or a non-reflecting fluid within said segment;
   flowing blood through the segment of the tubing;
   obtaining an infrared reflectance measurement of the segment of the tubing with said blood;
   deriving the natural log of the infrared reflectance measurement attributable to the presence of blood in the segment of the tubing;
   inputting the natural log of the infrared reflectance attributable to the blood in the segment of the tubing into a correlation equation to arrive at the hematocrit of the blood;
   outputting the predicted hematocrit of the blood.

2. The method of claim 1 further comprising a method for creating the correlation equation for a processing kit comprising:
   separately flowing a plurality of samples of blood through the segment of the tubing of the processing kit, each of the samples having a known hematocrit different from the hematocrit of the other samples;
   obtaining an infrared reflectance measurement of the segment of the tubing filled with blood for each sample;
   deriving the natural log of the infrared reflectance measurement attributable to the presence of blood in the segment of the tubing for each sample;
   deriving the correlation equation based on a linear fit of a plot of the known hematocrit for each sample and the natural log of the infrared reflectance measurement for each sample.

3. The method of claim 1 in which the correlation equation is developed at a time different from the processing of the blood and is pre-programmed into a controller for the reusable module.

4. The method of claim 2 in which the correlation equation is developed at a time different from the processing of the blood and is pre-programmed into a controller for the reusable module.

5. The method of claim 1 wherein the blood comprises whole blood.

6. The method of claim 2 wherein the blood comprises whole blood.

7. The method of claim 3 wherein the blood comprises whole blood.

8. The method of claim 4 wherein the blood comprises whole blood.

9. The method of claim 1 wherein the blood comprises concentrated red blood cells.

10. The method of claim 2 wherein the blood comprises concentrated red blood cells.

11. The method of claim 3 wherein the blood comprises concentrated red blood cells.

12. The method of claim 4 wherein the blood comprises concentrated red blood cells.

13. The method of claim 1 wherein the blood comprises a blood product including red blood cells.

14. The method of claim 2 wherein the blood comprises a blood product including red blood cells.

15. The method of claim 3 wherein the blood comprises a blood product including red blood cells.

16. The method of claim 4 wherein the blood comprises a blood product including red blood cells.

17. A reusable hardware module for use with a single-use processing kit for processing blood, the reusable module comprising:
   a programmable controller with an input for receipt of a first signal corresponding to an infrared reflectance measurement obtained from the processing kit and an output for transmitting a second signal corresponding to a predicted hematocrit for the blood being processed, the programmable controller being configured to derive the natural log of the infrared reflectance measurement, inputting the natural log of the infrared reflectance measurement into a predetermined correlation equation, generating the second signal corresponding to the predicted hematocrit, and transmitting the second signal to an interface.

* * * * *